United States Patent [19]

Baeten et al.

[11] Patent Number: 5,425,751
[45] Date of Patent: Jun. 20, 1995

[54] METHOD AND APPARATUS FOR OPTIMUM POSITIONING OF A MUSCLE STIMULATING IMPLANT

[75] Inventors: Cor X. Baeten, Maastricht; Antoine Camps, Wittem, both of Netherlands

[73] Assignee: Medtronic, Inc., Minneapolis, Minn.

[21] Appl. No.: 100,594

[22] Filed: Jul. 30, 1993

[51] Int. Cl.⁶ ............................................. A61N 1/04
[52] U.S. Cl. ........................... 607/28; 607/122; 607/132; 128/642; 128/733; 128/741
[58] Field of Search .............. 607/28, 119, 122, 132; 128/642, 733–735, 741

[56] References Cited

U.S. PATENT DOCUMENTS

| | | | |
|---|---|---|---|
| 3,682,162 | 8/1972 | Colyer | 128/642 |
| 3,757,790 | 9/1973 | Herrmann | 607/28 X |
| 4,245,643 | 1/1981 | Benzing, III et al. | 607/28 |
| 4,408,617 | 10/1983 | Auguste | 128/735 |
| 4,735,205 | 4/1988 | Chachques et al. | |

OTHER PUBLICATIONS

Center et al., "Measurement of Caridac Stimulation Threshold by Transcutaneous Needle Puncture" Journal of Throacic and Cardiovascular Surgery, v. 61 #5, May 1971, pp. 752–754.

Primary Examiner—Lee S. Cohen
Assistant Examiner—Jeffrey R. Jastrzab
Attorney, Agent, or Firm—Michael J. Jaro; Harold R. Patton

[57] ABSTRACT

A method and apparatus for determining the optimum location for implanting a muscle stimulating electrode. A test probe is provided for producing an electric current at various muscle tissue locations to determine comparative threshold measurements of the selected muscle tissue locations and determine the optimum location for implanting the muscle stimulating electrode.

16 Claims, 2 Drawing Sheets

METHOD AND APPARATUS FOR OPTIMUM POSITIONING OF A MUSCLE STIMULATING IMPLANT

BACKGROUND OF THE INVENTION

1. Field of the Invention

This invention relates generally a the method and apparatus for electrical muscle stimulation for various applications, including reconstructive cardiac surgery, and relates particularly to a method and apparatus for improving the function of a long-term muscle stimulating implant electrode.

2. Related Art

While much of prior art muscle stimulation techniques has been applied to cardiac muscles, other types of muscles have also been used, including those transplanted from one area of the body to another to improve the performance of an organ. One form of muscle stimulation apparatus for assisting cardiac muscle is disclosed in U.S. Pat. No. 4,735,205 ('205 patent), issued Apr. 8, 1988, to Juan C. Chachques, et al., and assigned to Medtronic, Inc. (also Assignee of the present invention).

The above identified '205 patent includes identification of a large group of related U.S. patent documents and other publications which provide a thorough identification of the background of the muscle stimulation art and are incorporated by reference in the present disclosure to provide suitable orientation information for practicing the present invention.

A problem associated with prior art muscle stimulation methods is determining a suitable location for placement of muscle stimulation electrodes which is close to the nerve branch to cause good excitability of the nerve and hence muscle, yet not so close that damage to the nerve occurs.

SUMMARY OF THE INVENTION

This invention relates to a method and apparatus for determining the optimum location for locating and implanting an intramuscular electrode in a selected muscle to produce the most efficient stimulation of that muscle. The muscle to be stimulated may consist in a myocardial substitute or merely another selected muscle in the body, either around the heart or elsewhere. A pulse generator, located outside of the sterile field, produces a measured electrical current to a test electrode or probe whereby a threshold measurement can be performed from outside the sterile field in order to determine the maximum muscle reaction to the current supplied through the test electrode to the selected muscular area. This produces comparative threshold measurements to determine the optimum location for the permanent implant electrode.

More specifically, this invention includes a method for determining the best implant location of a stimulating muscle electrode by engaging a test probe with various areas of the muscle tissue to provide comparative threshold measurements. A test pulse generator can be located outside the sterile field within the body and can be connected to a test probe such as a suture needle by a temporary conductor wire. Various areas of the muscle are tested to find the optimum reaction location. After finding this optimum location, the test conductor wire is severed, as with a pair of scissors. Thereafter, the operational stimulating implant electrode may be inserted into the muscular tissue to be stimulated at the determined optimum location.

A satisfactory procedure for inserting the stimulating electrode into the muscle is described in above-referenced '205 patent.

The apparatus embodying the present invention includes the use of a test electrode which can be in the form of a curved suture needle to which a temporary conductor wire is connected. The temporary conductor wire connects the test electrode to a generator located outside the sterile field. This provides means for measuring the current produced in the test electrode and permits determination of the maximum sensitivity threshold of the various test areas of the muscle being contracted by the test electrode. When the optimum sensitivity area is determined, the temporary conductor wire is severed, and the long-term muscle-pacing intramuscular electrode is then inserted into the muscle tissue at the optimum effective location.

There is provided in accordance with the present invention, a stimulation apparatus at least having:
    a stimulation electrode;
    a test probe connected to the stimulation electrode; and
    a conductive lead wired electrically connected to the test probe.

DETAILED DESCRIPTION OF THE DRAWINGS

Figure 1:
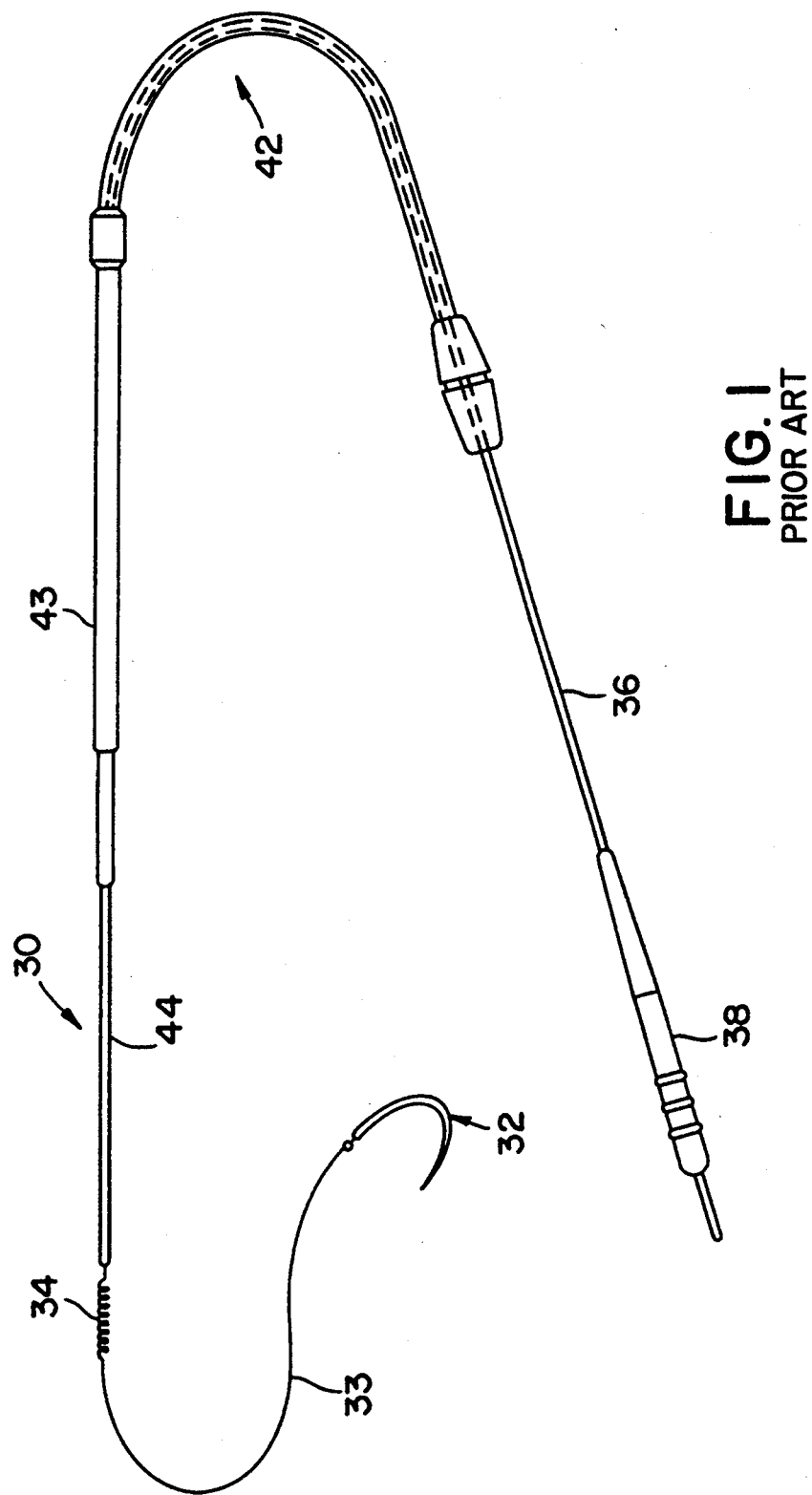
Figure 2:
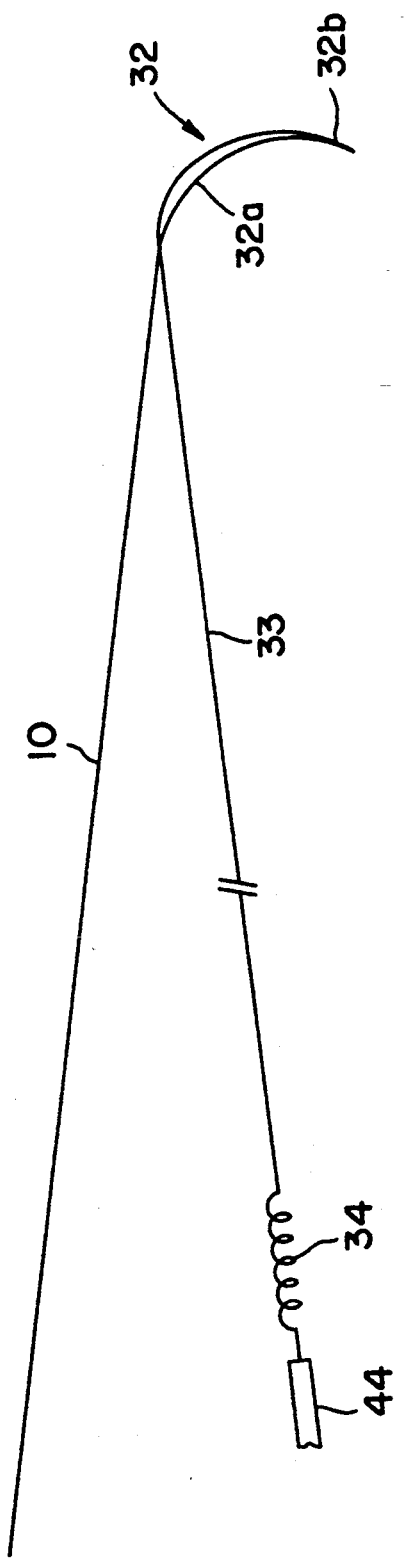

FIG. 1 is a schematic diagram of a prior art intramuscular lead, disclosed in U.S. Pat. No. 4,735,205; and FIG. 2 is a diagrammatic view, showing a response testing probe embodying the invention.

DETAILED DESCRIPTION OF THE BEST MODE OF THE INVENTION

Specific Background Disclosure of the Present Invention

In prior art U.S. Pat. No. 4,735,205 a suitable apparatus is disclosed in Columns 7 and 8 for electrical stimulation of a muscle. FIG. 4 of said prior art patent has been reproduced as FIG. 1 of the present disclosure to provide the necessary background information, as follows:

A pulse generator is coupled with an intramuscular lead 30 which includes the assembly of a suture needle 32, adapted to be drawn through the muscle to be implanted. A nonconductive line 33, having a coil 34 and a lead body 36 and connector 38 is provided along with a slidable insulating tube or sheath 42 lying over a portion of the insulated conductor 36 and the exposed electrode 44. The electrode 44 is implanted in the muscle by being drawn into the muscle by the nonconductive line 33 which is attached to the suture needle 32, which needle is inserted through the muscle. The connector 38 is adapted to be coupled to one of the output terminals of the pulse generator after the electrode 44 has been implanted in the muscle tissue (not shown) at an appropriate location.

DISCLOSURE OF THE PRESENT INVENTION

Prior to implanting the electrode 44, as described above, the present invention permits determining the optimum implant location. For determining the best location of the muscle implant electrode, threshold measurements at various test locations are carried out. One consideration in evaluating a location is whether that location requires only a low threshold stimulation signal (and hence low energy consumption) to cause muscle contraction, the locations with lowest thresholds being preferred locations. Another consideration in evaluating a location is whether stimulation at that location causes the muscle displacements/contractions to be large, the locations causing the largest muscle displacements being preferred locations. The two considerations are weighed while evaluating each location, in order to determine an optimum location.

These measurements can be obtained by positioning the distal end of a test electrode probe, such as a surgical needle 32, in contact with various test locations on the surface of a muscle. A temporary conductor wire 10 is provided for supplying test electrical current to the test probe 32. It has been found that the use of a sharp suture needle 32 provides the desired electrical contact with the surface of the muscle, or, in the alternative, the use of such a sharp probe element also permits inserting a short length of the sharp distal end of the needle 32 into the muscle, if desired. Because the probe needle 32 must be gripped by the surgeon during the testing of prospective implant electrode locations, the outside surface of the proximal gripping portion of the needle 32 spaced from the sharp muscle-contacting probe end thereof is provided with a suitable insulating coating 32a, such as a polyurethane adhesive, to prevent current leakage from the needle 32. The distal end 32b of the probe must make electrical contact with the muscle tissue being tested, and therefore is not insulated. It will be understood by those skilled in the art that the needle 32 need not necessarily be coated to be functional.

The use of the needle 32 for test stimulation of a muscle tissue area is accomplished by gripping the insulated surface 32a thereof and holding the uninsulated contact point area 32b in electrical contact with selected test areas of the muscle tissue. There is a risk of local tissue damage if the sharp point 32b of the needle 32 penetrates the surface of the muscle; therefore, non-penetrating contact has been found to be preferable to inserting the sharp end of the needle into the tissue of the muscle.

After testing the various prospective implant locations, and determining the optimum location, the temporary conductor wire 10 is cut adjacent to its attachment point with the needle and the needle 32 is then used by the surgeon to penetrate through the muscle and permit the electrode 44 of the muscle stimulator implant to be drawn into the optimum position of the for periodic stimulation, as described in the '205 patent.

In the preferred embodiment, the nonconductive line 33 is made of an absorbable (or bioabsorbable) suture material, so that it is eventually absorbed by the muscle tissue after implant. Such materials are known to those skilled in the art under such trademarks as Dexon TM, Vicryl TM, Maxon TM, and PDS TM.

Disclosure of an Alternate Embodiment of the Present Invention

In an alternative to the approach described above, the nonconductive line 33 is replaced with a thin conductive wire having an outer insulative coating, such as with the temporary conductor wire 10. The pin of the connector 38 is connected to a pulse generator. After the optimum electrode placement location is determined, as described supra., the electrode 44 is inserted in the muscle, followed by the cutting of the temporary conductor wire 10 at the end proximal to the suture needle 32 (outside the muscle).

It will be obvious to those skilled in the art that an implant electrode such as the electrode 44 may be used at numerous different muscle implant locations, and that the present invention is not limited to use with cardiomyoplasty. For example, the present invention can be used with a gracilis or gluteus muscle implant (not shown) to correct fecal incontinence or urinary incontinence. The present invention can also be used with a rectal muscle implant for bladder myoplasty or cardiomyoplasty.

We claim:

1. A stimulation electrode placement determination method for determining an optimum muscle tissue insertion location for a stimulation electrode, the method comprising the steps of:

providing a test probe to establish electrical contact with a selected portion of muscle tissue to be stimulated;

connecting a conductive lead wire to the test probe;

for several locations, imposing a threshold-measuring electric current on the test probe through the conductive lead wire to stimulate the muscle tissue;

for each of the locations, producing a threshold current measurement at which the muscle tissue reacts to the stimulation;

determining among the several locations, one which has an optimum muscular threshold reaction, and identifying it as the optimum location for permanent stimulation electrode implantation; and cutting the conductor wire leading to the test probe and inserting a stimulation electrode into the muscle tissue at the determined optimum location.

2. The method set forth in claim 1 wherein the step of providing a test probe to establish electrical contact with a selected portion of muscle tissue to be stimulated further comprises providing a suture needle coupled to a distal end of the stimulation electrode.

3. The method set forth in claim 1 wherein the step of providing a test probe to establish electrical contact with a selected portion of muscle tissue to be stimulated further comprises providing a suture needle in conductive relationship to the surface of the muscle tissue without full penetration of the surface.

4. The method set forth in claim 1 wherein the step of providing a test probe to establish electrical contact with a selected portion of muscle tissue to be stimulated further comprises providing a suture needle fully penetrating the surface of the muscle tissue.

5. A stimulation electrode placement determination arrangement for determining an optimum muscle tissue insertion location for a stimulation electrode comprising:

a stimulation electrode;

a test probe to establish electrical contact with a selected portion of muscle tissue to be stimulated;

a conductive lead wire connected to the test probe;

means for imposing a threshold-measuring electric current on the test probe through the conductive lead wire to stimulate the muscle tissue at several locations; and means for producing a threshold current measurement through the conductive lead wire at which the muscle tissue reacts to the stimulation at each of the locations; and a suture of absorbable material coupled between the test probe and the stimulation electrode wherein an implanter can determine among the several locations, one which has an optimum muscular threshold reaction, and identify it as the optimum location for permanent stimulation electrode implantation.

6. The arrangement set forth in claim 5 wherein the test probe is a suture needle distally coupled to said stimulation electrode.

7. The arrangement set forth in claim 6 wherein the suture needle comprises an insulating coating on its outer surface, the insulating coating terminating in spaced relation to a sharp end portion of the needle.

8. The arrangement set forth in claim 7 wherein the insulating coating comprises a polyurethane adhesive.

9. A stimulation apparatus comprising:
   a stimulation electrode;
   a test probe coupled to the stimulation electrode; and
   a conductive lead electrically coupled to the test probe; and
   a suture of absorbable material coupled between the test probe and the stimulation electrode.

10. The stimulation apparatus set forth in claim 9 wherein the test probe is a suture needle coupled to a distal end of the stimulation electrode.

11. The stimulation apparatus set forth in claim 10 wherein the suture needle comprises an insulating coating on its outer surface, the insulating coating terminating in spaced relation to a sharp end portion of the needle.

12. The stimulation apparatus set forth in claim 11 wherein the insulating coating comprises a polyurethane adhesive.

13. An apparatus for optimum positioning of a muscle stimulating implant comprising:
    a stimulation electrode;
    a test probe coupled to the stimulation electrode by a suture; and
    a conductive lead electrically coupled to the test probe.

14. The apparatus of claim 13 wherein the test probe is a suture needle having a sharp end portion.

15. The apparatus of claim 14 wherein the needle has an insulating coating on its outer surface, the insulating coating terminating in spaced relation to said sharp end portion of the needle.

16. The apparatus of claim 13 wherein the suture is constructed of an absorbable material.

* * * * *